United States Patent
Suzuki et al.

[11] Patent Number: 5,569,158
[45] Date of Patent: Oct. 29, 1996

[54] SHIELDING STRUCTURE OF ELECTRONIC ENDOSCOPE APPARATUS

[75] Inventors: Shigeo Suzuki; Fujio Okada, both of Omiya, Japan

[73] Assignee: Fuji Photo Optical Co. Ltd., Omiya, Japan

[21] Appl. No.: 313,363

[22] Filed: Sep. 27, 1994

[30] Foreign Application Priority Data

Oct. 15, 1993 [JP] Japan .................................. 5-281643

[51] Int. Cl.$^6$ ............................................ A61B 1/05
[52] U.S. Cl. ............................................ 600/110; 348/76
[58] Field of Search .................................. 600/110, 117, 600/118, 133; 348/72, 76; 361/91

[56] References Cited

U.S. PATENT DOCUMENTS

| | | | |
|---|---|---|---|
| 4,264,940 | 4/1981 | Castle | 361/91 |
| 4,607,621 | 8/1986 | Wheeler | 600/110 |
| 4,677,471 | 6/1987 | Takamura et al. | 600/134 |
| 4,759,346 | 7/1988 | Nakajima | 600/110 |
| 4,974,075 | 11/1990 | Nakajima | 600/110 |
| 5,136,250 | 8/1992 | Abdelli | 324/661 |
| 5,274,712 | 12/1993 | Lindsay et al. | 381/77 |

Primary Examiner—Richard J. Apley
Assistant Examiner—John P. Leubecker
Attorney, Agent, or Firm—Ronald R. Snider

[57] ABSTRACT

A shielding structure of an electronic endoscope apparatus which can sufficiently remove noise even when an electric cautery is used. A signal transmission cable which connects a charge coupled device disposed at the end portion of an electronic endoscope to a processor unit is electrically shielded by a double shield composed by an inner shield and an outer shield. The inner shield is connected to the ground in a light source connector and the outer shield is connected to the frame ground of the processor unit through a capacitor. The outer shield is further connected to a shielding member provided around the charge coupled device and a patient ground to which an electrode piece of an electric cautery is connected. Noise is greatly removed, so that the picture quality is improved.

5 Claims, 2 Drawing Sheets

SHIELDING STRUCTURE OF ELECTRONIC ENDOSCOPE APPARATUS

BACKGROUND OF THE INVENTION

This application claims the priority of Japanese Patent Application No. 5-281643 filed on Oct. 15, 1993, which is incorporated herein for reference.

1. Field of the Invention

The present invention relates to a shielding structure of an electronic endoscope apparatus provided with a charge coupled device at the end portion thereof to which an electric cautery can be introduced.

2. Description of the Related Art

An electronic endoscope apparatus is provided with a CCD (Charge Coupled Device) at the end portion of an electronic endoscope as a scope. The interior of the body is picked up by the CCD and the image is displayed on a monitor. An electric cautery or the like is introduced into the human body being observed through a medical instrument insertion channel provided in the electronic endoscope so as to resect or the like the deceased part by the electric cautery while observing the image on the monitor.

Since high-frequency noise is produced when the electric cautery is used, an electric shield is formed around the outer periphery of a signal transmission cable which is connected to the CCD so as to prevent the noise from mixing with a video signal or the like.

The conventional shielding structure, however, cannot be said to have a sufficient measure to counter noise, and when the electric cautery is used, noise often mixes with a video signal, which disturbs the image displayed on the monitor screen.

SUMMARY OF THE INVENTION

Accordingly, it is an object of the present invention to eliminate the above-described problem in the related art and to provide a shielding structure of an electronic endoscope apparatus which can sufficiently remove noise and therefore provide a clear image.

To achieve this aim, the present invention provides a shielding structure of an electronic endoscope apparatus for electrically shielding a signal transmission cable which connects a charge coupled device disposed at the end portion of an electronic endoscope to a processor unit; the shielding structure comprising;

an inner shield provided around the outer periphery of the signal transmission cable and connected to the ground in endoscope to a light source device and/or the ground in the processor unit; and an outer shield formed on the outside of the inner shield through an insulator and connected to the frame ground of the processor unit.

It is preferable that an electric shielding member is further provided in such a manner as to envelop the circuitry portion at the end of electronic endoscope at which the charge coupled device is disposed, that the shielding member is connected to the outer shield, and that the outer shield is connected to a patient ground to which an electrode piece of an electric cautery is connected.

It is further preferable that the outer shield is connected to the frame ground of the processor unit through a capacitor which maintains a predetermined withstand voltage.

According to this structure, since the high-frequency noise produced from an electric cautery or the like is caught by the double shield in the form of a noise current, and led to the frame ground of the processor unit. Since the high-frequency noise passing the outer shield is shielded by the inner shied, the noise entering the signal transmission cable is greatly reduced. If a capacitor is provided between the outer shield and the frame ground, the predetermined withstand voltage required in the electronic endoscope is maintained.

The above and other objects, features and advantages of the present invention will become clear from the following description of the preferred embodiment thereof, taken in conjunction with the accompanying drawings.

DESCRIPTION OF THE PREFERRED EMBODIMENT

Figure 1:
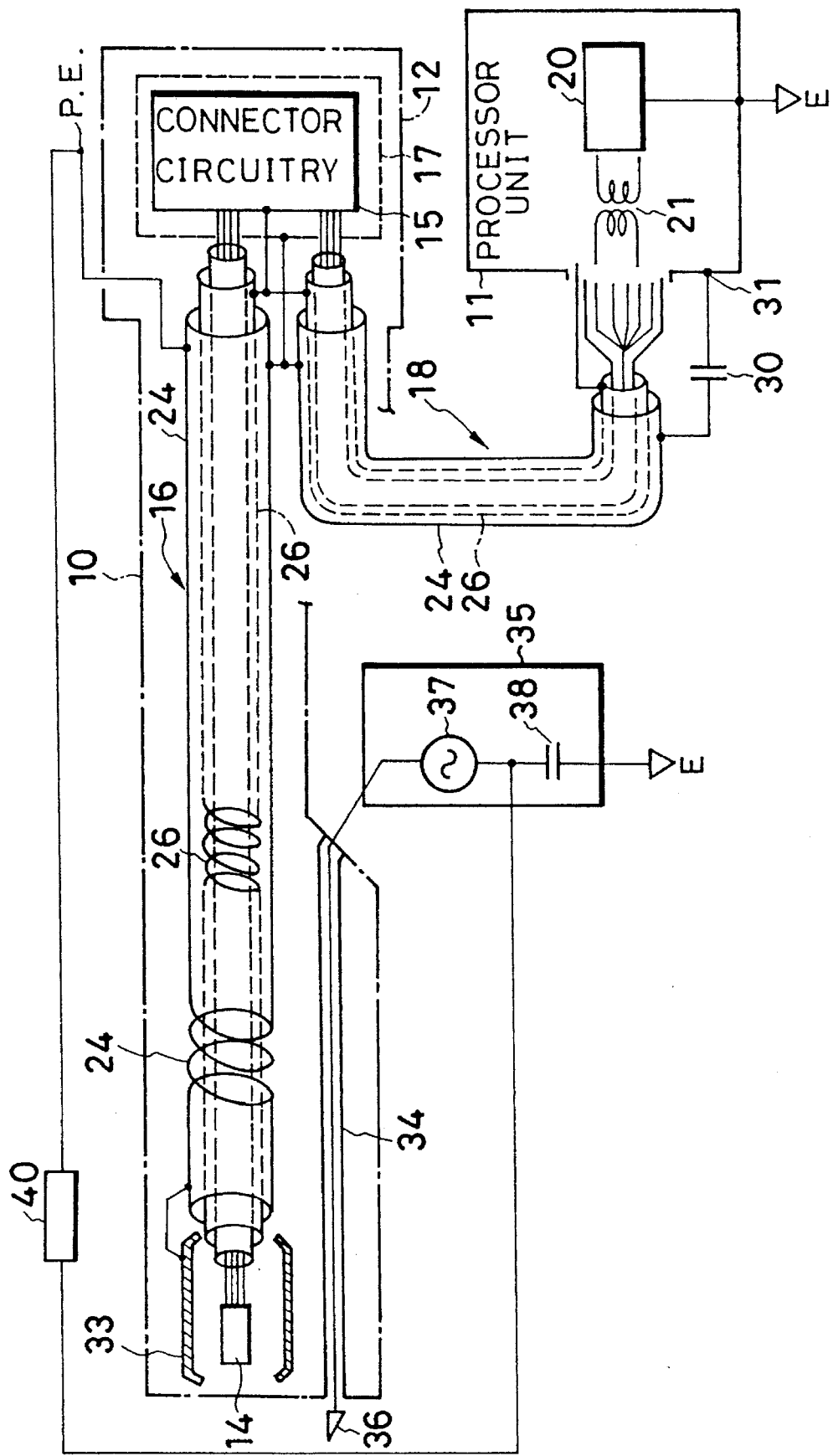
FIG. 1 shows the structure of an embodiment of a shielding structure of an electronic endoscope apparatus according to the present invention.
Figure 2:
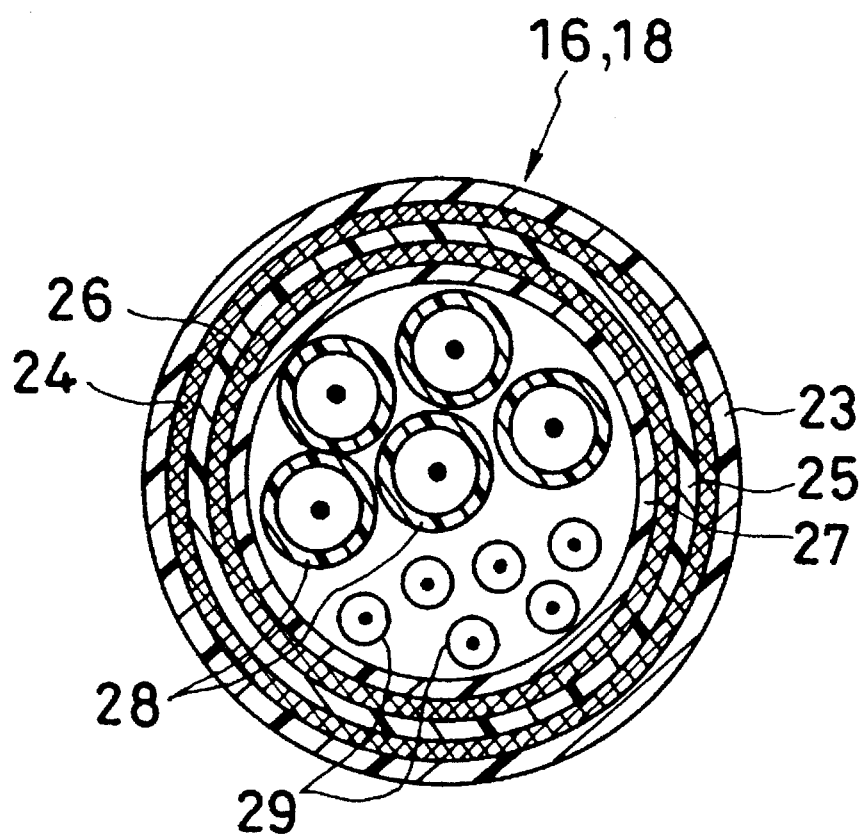
FIG. 2 is a sectional view of the internal structure of the signal transmission cables of the electronic endoscope apparatus shown in FIG. 1.

FIG. 1 shows the structure of an embodiment of a shielding structure of an electronic endoscope apparatus according to the present invention, and FIG. 2 is a sectional view of the signal transmission cables thereof. In FIG. 1, an electronic endoscope 10 as a scope is connected to a processor unit 11. In this embodiment, a light source connector 12 connects a light guide of the electronic endoscope 10 to a light source device (not shown). A CCD circuitry portion 14 composed of a CCD mounted on a circuit board is provided at the end portion of the electronic endoscope 10, and a signal transmission cable 16 is provided between the CCD circuitry portion 14 and a connector circuitry 15 within the light source connector 12. The connector circuitry 15 includes a circuit for driving the CCD and subjecting a video signal to amplification, gamma correction, etc., and the connector circuitry 15 is accommodated in an electrically shielded case 17. A signal transmission cable 18 is provided between the connector circuitry 15 and the processor unit 11. In the processor unit 11, the patient circuit such as the connector circuitry 15 is electrically isolated from an output of circuit 20 by an isolation device 21.

Each of the signal transmission cables 16 and 18 has a double shielding structure, as shown in FIG. 2. The double shielding structure is composed of an outer shield 24 including a coating 23 and a wound shielded wire, an insulator 25, an inner shield 26 constituted by a wound shielded wire, and an insulator 27. On the inside of the insulator 27, a coaxial wire 28 and a single wire 29 are disposed as signal wires. The outer shields 24 of the signal transmission cables 16, 18 are connected to the shielded case 17 of the light source connector 12, and both outer shields 24 are connected to each other, as shown in FIG. 1. Both the inner shields 26 are connected to the ground in the connector circuitry 15, and both inner shields 26 are connected to each other. The inner shields 26 of the cables 18 is connected to the circuit ground in the processor unit 11. The outer shields 24 are connected to the frame ground 31 of the processor unit 11 through a capacitor 30 having a withstand voltage of not less than 4 kV. In this embodiment, a shielding member 33 is further provided around the CCD circuitry portion 14, and the shielding member 33 is connected to the outer shields 24.

A medical instrument insertion channel 34 is provided in the electronic endoscope 10 so as to introduce an electric cautery 36 of an electric cautery device 35 to the end portion therethrough. The electric cautery device 35 is provided with a high-frequency current producer 37 for supplying high-frequency current to the end portion of the electric cautery 36 and a capacitor 38 having a floating capacity equivalent to that of the high-frequency current producer 37. One end of an electrode piece 40 which is placed on the back or the like of a patient is connected to the line between the high-frequency current producer 37 and the capacitor 38, and the other end of the electrode piece 40 is connected to a patient ground P.E. of the electronic endoscope 10 so as to feed back the leakage current in the electronic endoscope 10. The outer shield 24 of the signal cable 16 is connected to the patient ground P.E.

According to the structure of this embodiment, if the deceased part is positioned between the electrode piece 40 of the electric cautery device 35 and the electric cautery 36 which is introduced through the medical instrument insertion channel 34, resection by the electric cautery 36 is possible. When the electric cautery device 35 is in operation, a high-frequency noise current is caused on the outer shields of the signal transmission cables 16, 18 or the shielding member 33 around the CCD circuitry portion 14, but the noise current is guided to the frame ground 31 of the processor unit 11 through the capacitor 30, and further grounded. The noise current is also grounded through the patient ground P.E. The noise current produced on the inner shields 26 is introduced to the ground in the connector circuitry 15. Therefore, the noise current caused by the use of the electric cautery 36 is sufficiently removed by the double shielding structure constituted by the outer and inner shield 24, 26, so that the noise mixed with the video signal, the control signal or the like produced by the CCD is greatly reduced.

The capacitor 30 provided between the outer shields 26 and the frame ground 31 can float the signal transmission cables 16, 18 with respect to the ground at a withstand voltage of not less than 4 kV. Accordingly, the electronic endoscope 10 having these signal transmission cables 16, 18 adequately ensures the safety of a patient.

Although a double shielding structure is provided for both signal transmission cables 16, 18 in this embodiment, it is possible to provide the double shielding structure for only the signal transmission cable 16 and to shield the signal transmission cable 18 between the processor unit 11 and the light source connector 12 only with the inner shield 26.

As explained above, according to the present invention, a double electric shield is formed around the outer periphery of a signal transmission cable and the outer shield of the double electric shield is connected to the frame ground of a processor unit. As a result, noise is sufficiently removed even an electric cautery is used, so that a clear image is displayed on the monitor screen. In addition, since the outer shield is connected through a capacitor maintaining a predetermined withstand voltage, the electronic endoscope adequately ensures the safety of a patient in electricity.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. An electronic endoscope apparatus comprising:
   a signal transmission cable;
   a charge coupled device disposed at an end portion of the electronic endoscope signal transmission cable having an outer periphery;
   a processor unit having a circuit ground and a frame ground;
   an inner shield which is provided directly around said outer periphery of said signal transmission cable and which is constituted by wound shielded wire and connected to said ground in the processor unit;
   said inner shield having an insulator formed on the outside thereof;
   an outer shield formed outside of said inner shield insulator and connected to said frame ground of said processor unit; and
   a medical instrument insertion channel located outside of said outer shield.

2. An electronic endoscope apparatus according to claim 1, further comprising:
   a circuitry portion operating connected to the charge coupled device;
   an electric shielding member provided in such a manner as to envelop the circuitry portion and
   said electric shielding member being connected to said outer shield.

3. An electronic endoscope apparatus according to claim 1, further comprising an electric cautery, a patient ground and wherein said outer shield is connected to a patient ground to which an electrode piece of said electric cautery is connected.

4. An electronic endoscope apparatus according to claim 1, wherein said outer shield is connected to said frame ground of said processor unit through a capacitor which maintains a predetermined withstand voltage.

5. An electronic endoscope apparatus comprising:
   a processor unit having a frame ground;
   a charge coupled device;
   a signal transmission cable having an outer periphery and connecting the charge coupled device to the processor unit;
   a light source device;
   a light source connector having a ground;
   an inner shield which is provided directly around the outer periphery of said signal transmission cable;
   wherein said inner shield is constituted by wound shielded wire and connected to said ground in the light source connector;
   said inner shield having an insulator formed on the outside thereof;
   an outer shield formed outside of said inner shield insulator, and connected to the frame ground of said processor unit through a capacitor;
   a shielding member provided around said charge coupled device;
   a patient ground connected to an electrode piece of an electric cautery and connected to said shielding member provided around said charge coupled device; and a medical instrument insertion channel located outside of said outer shield.

* * * * *